United States Patent [19]

Peck et al.

[11] Patent Number: 5,981,524

[45] Date of Patent: *Nov. 9, 1999

[54] SUBSTITUTED 9-ALKYLADENINES

[75] Inventors: James V. Peck; Ronald J. Wysocki; Ibrahim M. Uwaydah; Noel J. Cusack, all of Richmond, Va.

[73] Assignee: Discovery Therapeutics, Inc., Richmond, Va.

[ * ] Notice: This patent is subject to a terminal disclaimer.

[21] Appl. No.: 08/904,553

[22] Filed: Aug. 4, 1997

Related U.S. Application Data

[63] Continuation of application No. 08/299,992, Sep. 1, 1994, Pat. No. 5,670,501.

[51] Int. Cl.[6] ............... C07D 473/34; C07D 317/72; A61K 31/52; A61K 31/535

[52] U.S. Cl. ............... 514/234.2; 514/261; 544/118; 544/277; 544/61

[58] Field of Search ............... 544/118, 61, 277; 514/234.2, 261

[56] References Cited

U.S. PATENT DOCUMENTS

| | | | |
|---|---|---|---|
| 3,929,763 | 12/1975 | Fauland et al. | 260/211.5 R |
| 3,989,833 | 11/1976 | Jonas et al. | 424/253 |
| 4,364,922 | 12/1982 | Berne et al. | 424/9 |
| 4,612,315 | 9/1986 | Jacobsen et al. | 514/263 |
| 4,714,697 | 12/1987 | Trivedi | 514/46 |
| 4,751,292 | 6/1988 | Fox | 536/24 |
| 4,853,386 | 8/1989 | Friebe et al. | 514/266 |
| 4,980,379 | 12/1990 | Belardinelli et al. | 514/821 |
| 5,066,655 | 11/1991 | Olsson | 514/261 |
| 5,117,830 | 6/1992 | McAfee et al. | 128/654 |
| 5,565,566 | 10/1996 | Olsson | 544/277 |

FOREIGN PATENT DOCUMENTS

| | | |
|---|---|---|
| 0 497 258 A2 | 8/1992 | European Pat. Off. . |
| 60-6616 | 6/1983 | Japan . |
| WO 90/09178 | 8/1990 | WIPO . |

OTHER PUBLICATIONS

Thompson, R.D. et al., "N[6],9–Disubstituted Adenines: Potent, Selective Antagonists at the $A_1$ Adenosine Receptor," *J. Med. Chem.* 34:2877–2882.

Barrett, R.J. et al., "Renal Hemodynamic and Excretory Effects of N–0861, a Non–Xanthine Adenosine $A_1$–Receptor Antagonist," *Drug Dev. Res.* 32:196–203 (1994).

Bertolet, B.D. et al., "Attenuation of Adenosine–Induced Chest Pain with N–0861 (N[6]–Endonorbornan–2–YL–9–Methyladenine), A Selective $A_1$ Adenosine Receptor Antagonist," Presented at the American College of Cardiology 43rd Annual Scientific Session (Mar. 1994).

Carstens, E. and Goldner, H., "6,9–Disubstituted purine derivatives," *Chem. Abstracts* 56:Abstract No. 10167i–10168d (1962).

Daly, J.W. et al., "Structure–Activity Relationships for N[6]–Substituted Adenosines at a Brain $A_1$–Adenosine Receptor with a Comparison to an $A_2$–Adenosine Receptor Regulating Coronary Blood Flow," *Biochem. Pharmacol.* 35(15):2467–2481 (1986).

(List continued on next page.)

*Primary Examiner*—Mark L. Berch
*Attorney, Agent, or Firm*—Sterne, Kessler, Goldstein & Fox P.L.L.C.

[57] ABSTRACT

Optically active or racemic compounds represented by the formula

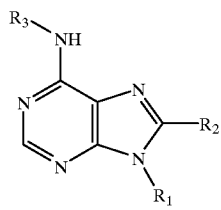

where $R_1$ is $C_1$ to $C_4$ straight chain or branched alkyl; $R_2$ is selected from the group consisting of H, —$OR_1$, —$SR_1$, —$NH(R_1)$, —$N(R_4)(R_5)$, aminocarbonyl, halogen, and —CN, where $R_4$ and $R_5$ are independently $C_1$ to $C_6$ straight chain or branched alkyl, or taken together form a 3- to 7-membered heterocycloalkyl substituent, such heteroatom selected from the group consisting of oxygen, nitrogen and sulfur, optionally including an additional heteroatom which is selected from the group consisting of nitrogen, oxygen, and sulfur; $R_3$ is cyclopentyl or:

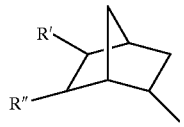

where R' and R" are independently H, =O, —OH, or —$NH_2$, with the proviso that R' and R" can be taken together form the following structure as $R_3$:

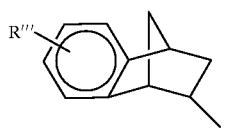

where R'" is —OH or —$NH_2$; and with the further proviso that when $R_3$ is cyclopentyl or norbornyl, then $R_2$ cannot be H or halogen; and pharmaceutically-acceptable salts thereof.

These compounds are useful as diuretics, renal protectives against acute or chronic renal failure, as well as agents to facilitate recovery from coma, to improve the therapeutic outcome resulting from defibrillation or cardiopulmonary resuscitation by preventing post-resuscitation bradycardia, bradyarrhythmia and cardioplegia, to restore cardiac function following a cardioplegic procedure, and to treat or prevent intermittent claudication.

13 Claims, No Drawings

OTHER PUBLICATIONS

"Gensia's Protara Fails to Demonstrate Efficacy in Confirmitory Study," *Genetic Engineering News*, p. 32 (Nov. 1, 1994).

Jacobson, K.A. et al., "[$^3$H]Xanthine amine cogener of 1,3–dipropyl–8–phenylxanthine: An antagonist radioligand for adenosine receptors," *Proc. Nat'l Acad. Sci. USA* 83:4089–4093 (1986).

Jacobson, K.A. et al., "Adenosine Receptors: Pharmacology, Structure–Activity Relationships, and Therapeutic Potential," *J. Med. Chem.* 35(3):407–422 (1992).

Martin, P.L. et al., "(±)–N$^6$–Endonorbornan–2–yl–9–Methyladenine (N–0861) and its Enantiomers: Selective Antagonists of $A_1$–Adenosine Receptors in Guinea Pig Isolated Atria," *J. Pharm. Expt. Therap.* 265(1):201–206 (Apr. 1993).

Rose, J. et al., "Safety, Tolerability, Renal Effects and Pharmacokinetics in Man of Single Doses of FK453, a Novel Adenosine $A_1$ Receptor Antagonist," Presented at the British Pharmacological Society Meeting, Abstract No. P149 (1991).

Shimada, J. et al., "8–(Dicyclopropylmethyl)–1,3–dipropylxanthine: A Potent and Selective Adenosine $A_1$ Antagonist with Renal Protective and Diuretic Activities," *J. Med. Chem.* 34(1):466–469 (1991).

Stein, H.H. and Somani, P., "Cardiovascular Effects of Nucleoside Analogs," *Ann. NY Acad. Sci.* 255:380–389 (1975).

Stiles, G.L., "Adenosine receptors: structure, function and regulation," *TIPS Reviews*:486–490 (Dec. 1986).

Terai, T. et al., "The renal effects of FR–113453, a potent non–xanthine adenosine antagonist," *XIth Intl. Cong. of Pharmacol.*, Amsterdam, the Netherlands, Abstract No. P.tu.435 (Jul. 2–6 1990).

Thompson, R.D. et al., "N$^6$,9–Disubstituted Adenines: Potent, Selective Antagonists at the $A_1$ Adenosine Receptor," *J. Med. Chem.* 34(9):2877–2882 (1991).

Ukena, D. et al., "Species differences in structure–activity relationships of adenosine agonists and xanthine antagonists at brain A1 adenosine receptors," *FEBS Lett.* 209(1):122–128 (1986).

Ukena, D. et al., "Definition of subclasses of adenosine receptors associated with adenylate cyclase: interaction of adenosine analogs with inhibitory $A_1$ receptors and stimulatory $A_2$ receptors," *Can. J. Physiol. Pharmacol.* 65:365–376 (1987).

Ukena, D. et al., "N$^6$–substituted 9–methyladenines: a new class of adenosine receptor antagonists," *FEBS Lett.* 215(2):203–208 (1987).

Wesley, R.C. et al., "Effect of selective $A_1$ adenosine receptor antagonism of postdefibrillation cardiovascular depression: evidence for an antiadrenergic role of endogenous adenosine," *Cardiovascular Res.* 27:129–133 (1993).

Williams, M., "Adenosine Antagonists," *Med. Res. Rev.* 9(2):219–243 (1989).

SUBSTITUTED 9-ALKYLADENINES

This application is a continuation of application Ser. No. 08/299,922, filed Sep. 1, 1994, U.S. Pat. No. 5,670,501.

FIELD OF THE INVENTION

This invention generally relates to novel substituted 9-alkyladenine compounds, to processes for preparing such compounds, and methods for administering compositions of such compounds in amounts effective to induce a desired physiological response in mammals involving the antagonism of adenosine receptors. More particularly, this invention relates to compounds for therapeutic use, in particular as diuretics, renal protectives against acute or chronic renal failure, as well as agents to facilitate recovery from coma, to treat or prevent intermittent claudication, to restore cardiac function following a cardioplegic procedure, and to improve the therapeutic outcome resulting from defibrillation or cardiopulmonary resuscitation by preventing post-resuscitation bradycardia, bradyarrhythmia and cardioplegia.

BACKGROUND OF THE INVENTION

Adenosine (9-β-D-ribofuranosyl-9H-purin-6-amine) was characterized in the late 1920's as having hypotensive and bradycardic activity. Since then, considerable research in the molecular modification of adenosine has led to the general conclusion that cardiovascular activity is limited to analogs having intact purine and β-ribofuranosyl rings.

Further research more clearly defined how the activity of these adenosine analogs affected the purinergic receptors in peripheral cell membranes, particularly the $A_1$ and $A_2$ receptors.

Adenosine antagonists have helped explain the role of adenosine in various physiological processes. Specifically, selective antagonists for the adenosine $A_1$ receptor were critical in defining the physiological importance of $A_1$ receptor activation. Non-selective adenosine antagonists such as caffeine and theophylline served as starting points for structure activity research with the goal of creating $A_1$ receptor selective antagonists. An example of such a discovery is 8-(Dicyclopropylmethyl)-1,3-dipropylxanthine (Shimada, J., et al., *J. Med. Chem.*, 34:466–9 (1991)). Alternatively, various non-xanthine adenosine antagonists have been identified, including triazolo[4,3-a]quinoxalinamines, triazoloquinazolines, pyrazolo[4,3-d]pyrimidin-7-ones, and adenine derivatives (Williams, M., *Med. Res. Rev.*, 9(2):219–43 (1989)). A series of adenine derivatives was identified in U.S. Pat. No. 5,066,655. The search continues for potent and selective adenosine $A_1$ receptor selective antagonists, useful as pharmacological tools and as therapeutic agents.

SUMMARY OF THE INVENTION

Certain novel compounds have now been discovered having activity as adenosine antagonists. These compounds have the structural Formula (I):

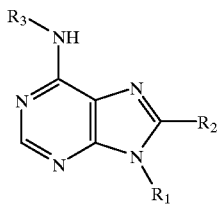

I where $R_1$ is $C_1$ to $C_4$ straight chain or branched alkyl; $R_2$ is selected from the group consisting of H, —$OR_1$, —$SR_1$, —$NH(R_1)$, —$N(R_4)(R_5)$, aminocarbonyl, halogen, and —CN, where $R_4$ and $R_5$ are independently $C_1$ to $C_6$ straight chain or branched alkyl, or taken together form a 3- to 7-membered heterocycloalkyl substituent, the heteroatom selected from the group consisting of nitrogen, oxygen and sulfur, optionally including an additional heteroatom which is selected from the group consisting of nitrogen, oxygen, and sulfur; $R_3$ is cyclopentyl or:

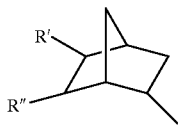

where R' and R" are independently H, =O, —OH, or —$NH_2$, with the proviso that R' and R" can be taken together to form the following structure as $R_3$:

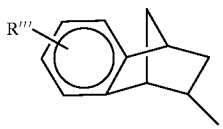

where R'" is —OH or —$NH_2$; and with the further proviso that when $R_3$ is cyclopentyl or norbornyl, then $R_2$ cannot be H or halogen.

In the above adenine-related compounds of the present invention, it is preferred that $R_1$ is $C_1$ to $C_4$ lower or branched alkyl, most preferably methyl or ethyl.

In the preferred compounds, it is preferred that $R_2$ is hydrogen, halogen, cyano, lower ($C_1$ to $C_4$ lower or branched) alkoxy or lower alkylthio, amino or amino substituted with lower alkyl, cycloalkyl or heterocyclic alkyl. In the preferred compounds it is most preferred that $R_3$ is endo-2-norbornyl substituted in the 5-position (i.e., R') in an endo orientation with hydroxy or amino; or that $R_3$ is cyclopentyl.

The compounds of the present invention are all therapeutically effective adenosine receptor antagonists in mammals. Thus, they are effective for treating conditions that respond to selective adenosine $A_1$ receptor blockade. Accordingly, the compounds of the present invention are useful as diuretics, renal protectives against acute or chronic renal failure, as agents for facilitating recovery from coma (to induce awakening and higher levels of consciousness), to restore cardiac function following a cardioplegic procedure, and to treat or prevent intermittent claudication (angina of the skeletal muscle arising from hypoxia), and as agents to improve the therapeutic outcome resulting from cardiac defibrillation or cardiopulmonary resuscitation.

DETAILED DESCRIPTION OF THE PREFERRED EMBODIMENTS

Illustrative compounds of the present invention having Formula I include, but are not limited to: (±)-$N^6$-(endo-2'- norbornyl)-8-isopropylmethylamino-9-methyladenine, $N^6$-cyclopentyl-8-isopropylmethylamino-9-methyladenine, (±)-$N^6$-[endo-2'-(endo-5'-hydroxy)norbornyl]-9-methyladenine, (±)-$N^6$-[endo-2'-(endo-5'-hydroxy) norbornyl]-8-isopropylmethylamino-9-methyladenine, (±)-$N^6$-[endo-2'-(endo-5'-hydroxy)norbornyl]-8-bromo-9-methyladenine, $N^6$-cyclopentyl-8-methylthio-9-methyladenine, (±)-$N^6$-[endo-2'-norbornyl]-8-methylthio-9-methyladenine, (±)-$N^6$-[endo-2'-(endo-5'-hydroxy) norbornyl]-8-dimethylamino-9-methyladenine, (±)-$N^6$-(endo-2'-norbornyl)-8-cyano-9-methyladenine, (±)-$N^6$-(endo-2'-norbornyl)-8-methoxy-9-methyladenine, (±)-$N^6$-(endo-2'-norbornyl)-8-dimethylamino-9-methyladenine, (±)-$N^6$-[endo-2'-(5'-keto)norbornyl]-8-bromo-9-methyladenine, (±)-$N^6$-(endo-2'-norbornyl)-8-diethylamino-9-methyladenine, (±)-$N^6$-(endo-2'-norbornyl)-8-piperidinyl-9-methyladenine, (±)-$N^6$-(endo-2'-norbornyl)-8-amido-9-methyladenine, (±)-$N^6$-[endo-2'-(5', 6'-(6"-hydroxy)benzo) norbornyl]-9-methyladenine, (±)-$N^6$-[endo-2'-(endo-5'-hydroxy)norbornyl]-9-methyladenine, and $N^6$-cyclopentyl-8-dimethylamino-9-methyladenine. The above compounds are illustrative only and are not meant to be limiting in any way.

Typical 3- to 7-membered heterocyclic substituents which may be represented by $R_2$ include aziridinyl, piperidinyl, piperazinyl, pyrrolidinyl, imidazolidinyl, imidazolinyl, morpholinyl, pyrazolidinyl, pyrazolinyl and the like.

Typical halo groups include fluorine, chlorine, bromine, and iodine.

Typical $C_{1-6}$ alkyl groups include methyl, ethyl, propyl, isopropyl, butyl, sec.-butyl, tert.-butyl, pentyl and hexyl groups.

Compositions within the scope of this invention include all compositions wherein the compounds of the present invention are contained in an amount that is effective to achieve its intended purpose. While individual needs vary, determination of optimal ranges of effective amounts of each component is with the skill of the art. Typically, the compounds may be administered to mammals, e.g., humans, orally at a dose of 0.001 to 100 mg/kg, or an equivalent amount of the pharmaceutically acceptable salt thereof, per day of the body weight of the mammal being treated for diuresis, bradycardia, bradyarrhythmia and cardioplegia after cardiopulmonary resuscitation or when the compounds are administered as renal protectives. Preferably, about 0.01 to about 10 mg/kg is orally administered to treat or prevent such disorders. For intramuscular injection, the dose is generally about one-half of the oral dose. For example, a suitable intramuscular dose is about 0.0005 to about 50 mg/kg, and most preferably, from about 0.05 to about 5 mg/kg. For intravenous administration, the dose is generally 0.0001 to about 10 mg/kg, and most preferably, from about 0.001 to about 1 mg/kg.

The unit oral dose can comprise from about 0.1 to about 7000 mg, preferably about 1 to about 700 mg of the compound. The unit dose can be administered one or more times daily as one or more tablets each containing from about 0.1 to about 500, conveniently about 0.1 to 100 mg of the compound or its solvates.

In addition to administering the compound as a raw chemical, the compounds of the invention can be administered as part of a pharmaceutical preparation containing suitable pharmaceutically acceptable carriers comprising excipients and auxiliaries that facilitate processing of the compounds into preparations that can be used pharmaceutically. Preferably, the preparations, particularly those preparations that can be administered orally and that can be used for the preferred type of administration, such as, tablets, dragees, and capsules, and preparations that can be administered rectally, such as, suppositories, as well as suitable solutions for administration by injection or orally, contain from about 0.01 to 99 percent, preferably from about 0.25 to 75 percent, of active compound(s), together with the excipient.

Also included within the scope of the present invention are the non-toxic pharmaceutically acceptable salts of the compounds of the present invention. Salts are formed by mixing a solution of the particular compound of the present invention with a solution of a pharmaceutically acceptable non-toxic acid, such as hydrogen chloride, acetic acid, malic acid, phosphoric acid and the like.

The pharmaceutical compositions of the invention can be administered to any mammal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal or buccal routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically. Preferably, the preparations, particularly those preparations that can be administered orally and that can be used for the preferred type of administration, such as, tablets, dragees, and capsules, and also preparations which can be administered rectally, such as, suppositories, as well as suitable solutions for administration by injection or orally, are present at a concentration of from about 0.01 to 99 percent, together with the excipient.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules, which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and obvious to those skilled in the art are within the spirit and scope of the invention.

EXAMPLES

Compounds of the present invention wherein $R_1$ is lower alkyl can be prepared as shown below (Method A, where $R_1$ is $CH_3$). The process is described in detail in Example #13.

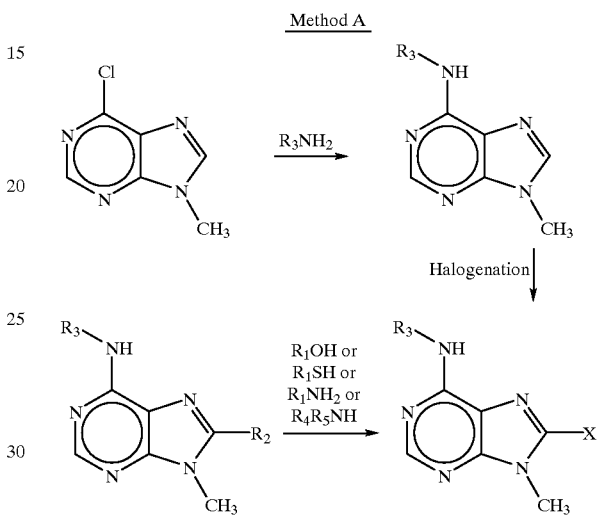

Method A

Method A—Detailed Example: Preparation of (±)-$N^6$-(endo-2'-norbornyl)-8-isopropylmethylamino-9-methyladenine.

A solution of 2 gm (5.42 mmol) of (±)-$N^6$-(endo-2'-norbornyl)-8-iodo-9-methyladenine (prepared by halogenation of (±)-$N^6$-(endo-2'-norbornyl)-9-methyladenine (U.S. Pat. No. 5,066,655) substantially according to Moriarty, R. M., et al., *Tet. Lett.*, 31:5887–90 (1990)) in 5 ml (47 mmol) of N-methylisopropylamine was heated to 135° C. overnight in a reaction bomb. After cooling, the reaction mixture was dissolved in dichloromethane and with water. The organic phase was dried ($MgSO_4$), filtered and concentrated. The residue was chromatographed on a silica gel column (ethyl acetate/hexane (1:1); followed by ethyl acetate) to afford the product, which was converted to the maleate salt to afford 347 mg of a light yellow solid.

TABLE 1

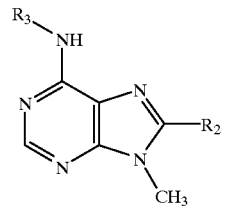

| Example | $R_2$ | $R_3$ | Elemental Formula | Elemental Analysis (calc./obs.) |
|---|---|---|---|---|
| 1 | —CN | endo- | $C_{14}H_{16}N_6$/ | C: 56.24/56.67 |

TABLE 1-continued

[Structure: purine ring with R3-NH at 6-position, R2 at 8-position, CH3 on N9]

| Example | R₂ | R₃ | Elemental Formula | Elemental Analysis (calc./obs.) |
|---|---|---|---|---|
| | | norbornyl | C₄H₄O₄ | H: 5.24/5.43<br>N: 21.86/22.11 |
| 2 | —C(=O)—NH₂ | endo-norbornyl | C₁₄H₁₈N₆O | C: 58.73/58.52<br>H: 6.34/6.17<br>N: 29.40/28.86 |
| 3 | —SCH₃ | endo-norbornyl | C₁₄H₁₉N₅S/<br>C₄H₄O₄ | C: 53.22/53.16<br>H: 5.28/5.72<br>N: 17.27/17.09 |
| 4 | —OCH₃ | endo-norbornyl | C₁₄H₁₉N₅O/<br>C₄H₄O₄ | C: 55.52/55.74<br>H: 5.95/6.01<br>N: 17.98/18.10 |
| 5 | —N(CH₃)₂ | endo-norbornyl | C₁₅H₂₂N₆/<br>C₄H₄O₄ | C: 56.71/56.93<br>H: 6.51/6.28<br>N: 20.88/20.92 |
| 6 | —N(morpholino) | endo-norbornyl | C₁₇H₂₄N₆O/<br>C₄H₄O₄ | C: 56.75/56.80<br>H: 6.35/6.24<br>N: 18.91/18.89 |
| 7 | —N(pyrrolidinyl) | endo-norbornyl | C₁₇H₂₄N₆/<br>C₄H₄O₄ | C: 58.87/59.01<br>H: 6.59/6.85<br>N: 19.61/20.12 |
| 8 | —N(CH₃)₂ | cyclopentyl | C₁₃H₂₀N₆ | C: 59.97/59.71<br>H: 7.74/7.42<br>N: 32.28/32.56 |
| 9 | —N(thiomorpholino) | endo-norbornyl | C₁₇H₂₄N₆S/<br>C₄H₄O₄ | C: 54.77/54.71<br>H: 6.13/6.28<br>N: 18.25/17.90 |
| 10 | —N(CH₂CH₃)₂ | endo-norbornyl | C₁₇H₂₆N₆/<br>C₄H₄O₄ | C: 58.59/58.68<br>H: 7.02/7.06<br>N: 19.52/19.64 |
| 11 | —N(CH₃)[(CH₂)₃CH₃] | endo-norbornyl | C₁₈H₂₈N₆/<br>C₄H₄O₄ | C: 59.44/59.55<br>H: 7.26/7.26<br>N: 18.91/19.05 |
| 12 | —SCH₃ | cyclopentyl | C₁₂H₁₇N₅S | C: 54.72/54.77<br>H: 6.51/6.51<br>N: 26.59/26.59 |
| 13 | —N(CH₃)(CH(CH₃)₂) | endo-norbornyl | C₁₇H₂₆N₆/<br>C₄H₄O₄ | C: 58.59/58.34<br>H: 7.02/7.08<br>N: 19.52/19.33 |
| 14 | —N(CH₂CH₃)₂ | cyclopentyl | C₁₅H₂₄N₆/<br>1/3 H₂O | C: 61.19/61.21<br>H: 8.45/8.45<br>N: 28.55/28.55 |

TABLE 1-continued

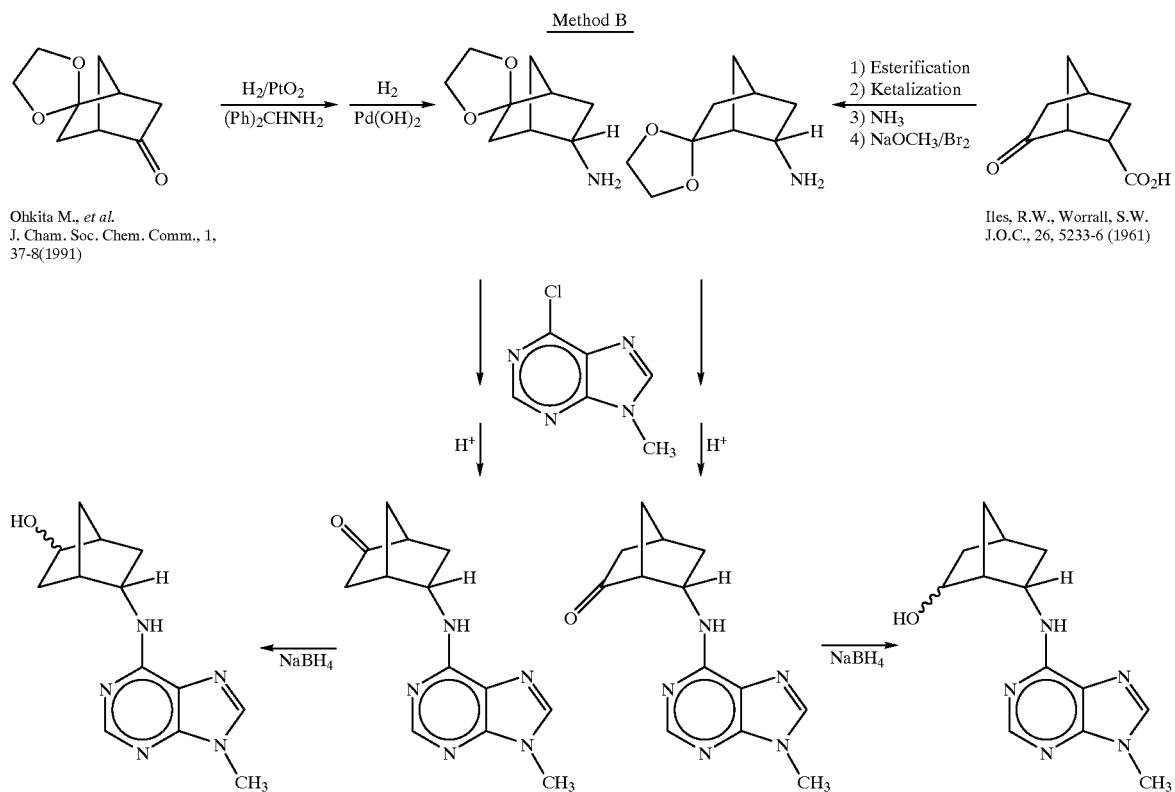

| Example | $R_2$ | $R_3$ | Elemental Formula | Elemental Analysis (calc./obs.) |
|---|---|---|---|---|
| 15 | —N(morpholine) | cyclo-pentyl | $C_{15}H_{22}N_6O$ | C: 59.58/59.60<br>H: 7.33/7.48<br>N: 27.79/27.91 |

Note: The 8-cyano derivative was prepared by displacement of the 8-halo intermediate in Method A, and the 8-amido derivative was prepared by oxidation of the 8-cyano compound with sulfuric acid under standard conditions.

Compounds of the present invention, wherein $R_1$ is illustrated by $CH_3$ a substituted norbornyl group as defined in Table II, can be prepared as show below (Method B). The process is described in detail in Example #21.

A. endo-2-aminonorbornan-5-one ethylene ketal. A two-liter Parr bottle was charged with 210 gm (1.25 mol) norbornan-2,5-dione monoethylene ketal (Ohkita, M., etal., *J. Chem. Soc. Chem. Comm.* 1:37–38 (1991)), 238.3 gm In order to prepare derivatives in Table II where $R_2$ is not H, the above substituted norbornanones are halogenated, e.g., with chlorine, and reacted as depicted in the last two steps of Method A.

Method B—Detailed Example: Preparation of (±)-$N^6$-[endo-2'-(endo-5'-hydroxy)-norbornyl]-9-methyladenine.

(1.25 mol) aminodiphenylmethane, 108 ml (1.9 mol) acetic acid, and 1.2 liters methanol. Under nitrogen, 6.3 g platinum (IV) oxide was added to the mixture, and this was placed on a Parr apparatus under 50 psi hydrogen. This reaction mixture was shaken at room temperature for 2 hours, whereupon the calculated amount of hydrogen uptake was reached. Filtration and concentration on a rotary evaporator gave 494.4 gm (quantitative yield). A 2 liter Parr bottle was charged with this product, 1.2 liters methanol and 17.5 gm palladium hydroxide under nitrogen. This mixture was hydrogenated on a Parr apparatus for six hours at 68° C. under 40 psi hydrogen, and then the reaction was allowed to cool by shaking overnight at room temperature. The catalyst was removed by filtration, and the filtrate was concentrated to yield a paste-like residue. Trituration with diethyl ether and drying yielded 212.2 gm (74%) of endo-2-aminonorbornan-5-one ethylene ketal acetate.

B. (±)-$N^6$-[endo-2'-aminonorboman-5one]-9-methyladenine. A 5 liter four-necked round bottom flask equipped with a mechanical stirrer and condenser with attached nitrogen bubbler was charged with 201.4 gm (0.88 mol) endo-2-aminonorbornan-5-one ethylene ketal acetate, 151.7 gm (0.9 mol) 6-chloro-9-methylpurine, 364.3 gm (3.6 mol) triethylamine, 3 gm tetrabutylammonium iodide, and 2 liters of 1-propanol. This was heated at reflux overnight with stirring, then cooled to room temperature. The mixture was filtered and concentrated under reduced pressure to a thick brown syrup. Trituration of the syrup with diethyl ether gave 207.8 gm (78%) of a solid product. A 250 ml round bottom flask was charged with 58.8 gm (0.195 M) of this material, 195 ml 3 N HCl, and 120 ml methanol. This mixture was heated on a steam bath for 30 minutes, and then was concentrated under reduced pressure. The residue was partitioned between saturated aq. potassium carbonate and dichloromethane. Two organic extracts (2×300 ml methylene chloride) were pooled, dried with magnesium sulfate, and concentrated to give 52.9 gm (quantitative yield) of a pale brown viscous oil, which solidified on standing.

C. (±)-$N^6$-[endo-2'-(endo-5'-hydroxy)-norbornyl]-9-methyladenine.

A 1 liter round bottom flask was charged with 48.9 gm (0.18 M) of the above compound dissolved in 490 ml methanol. This mixture was cooled in a water bath to,about 15° C., whereupon 3.5 gm (0.09 M) sodium borohydride was added all at once with stirring, and the reaction mixture was let stir overnight. A solid (23.6 gm) had formed overnight, and was removed by filtration. The volume of the methanol filtrate was reduced to about 175 ml by warming under a nitrogen stream. Upon cooling, a second crop of crystals was obtained (5.2 gm). The combined solid products were dissolved with warming in methanol, treated with charcoal, and filtered. The filtrate was reduced to a minimal volume with which to filter the final solid product, which upon drying resulted in 23.7 gm (50.8%) of product.

TABLE II

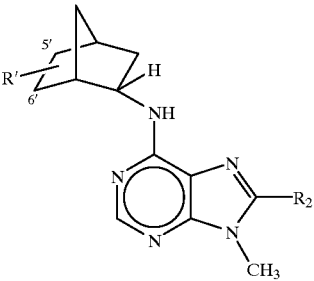

| Example | R' | $R_2$ | Empirical Formula | Elemental Analysis (calc./obs.) |
|---|---|---|---|---|
| 16 | 5'-endo-OH | 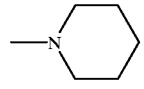 | $C_{17}H_{26}N_6O$ | C: 61.79/61.70<br>H: 7.93/7.78<br>N: 25.43/25.37 |
| 17 | 5'-endo-OH | Br | $C_{13}H_{16}BrN_5O$ | C: 46.17/46.11<br>H: 4.77/4.93<br>N: 20.71/20.56 |
| 18 | 5'-endo-OH | —$N(CH_3)_2$ | $C_{15}H_{22}N_6O$ | C: 59.58/59.33<br>H: 7.33/7.39<br>N: 27.79/27.60 |
| 19 | 6'-keto | Br | $C_{13}H_{14}N_5OBr$/ ¼ $C_4H_8O_2$ | C: 46.94/46.76<br>H: 4.50/4.75<br>N: 19.55/19.85 |
| 20 | H | piperidinyl | $C_{18}H_{26}N_6$/ $C_4H_4O_4$ | C: 59.71/59.95<br>H: 6.83/7.00<br>N: 18.99/19.14 |
| 21 | 5'-endo-OH | H | $C_{13}H_{17}N_5O$ | C: 60.21/60.00<br>H: 6.61/6.55<br>N: 27.01/26.85 |

TABLE II-continued

[Structure: norbornane-NH-purine with R' at 5'/6' and R2 at imidazole, N-CH3]

| Example | R' | R2 | Empirical Formula | Elemental Analysis (calc./obs.) |
|---|---|---|---|---|
| 22 | 5'-exo-OH | H | $C_{13}H_{17}N_5O$/ 1¼ $H_2O$ | C: 55.40/55.79<br>H: 6.97/6.96<br>N: 24.85/24.53 |
| 23 | 6'-exo-OH | H | $C_{13}H_{17}N_5O$/ ¼ $H_2O$ | C: 59.18/59.36<br>H: 6.69/6.78<br>N: 26.55/26.44 |
| 24 | 6'-endo-OH | H | $C_{13}H_{17}N_5O$ | C: 60.21/60.11<br>H: 6.61/6.73<br>N: 27.01/26.84 |
| 25 | 5'-endo-OH | —N(morpholine) | $C_{17}H_{24}N_6O_2$/ $C_4H_4O_4$ | C: 54.76/54.60<br>H: 6.13/6.11<br>N: 18.25/18.11 |
| 26 | 5'-endo-OH | —NCH(CH3)2 | $C_{16}H_{24}N_6O$/ $C_4H_4O_4$ | C: 55.55/55/46<br>H: 6.53/6.35<br>N: 18.25/18.11 |
| 27 | 5'-exo-OH | Br | $C_{13}H_{16}N_5OBr$ | C: 46.16/46.30<br>H: 4.76/5.00<br>N: 20.71/20.54 |
| 28 | 6'-keto | —N(CH3)2 | $C_{15}H_{20}N_6O$ | C: 59.98/59.75<br>H: 6.71/6.66<br>N: 27.98/27.75 |
| 29 | 5'-keto | H | $C_{13}H_{15}N_5O$/ $C_4H_4O_4$ | C: 54.69/54.90<br>H: 5.13/5.26<br>N: 18.76/18.95 |

Compounds of the present invention, wherein $R_1$ is illustrated by $CH_3$ and $R_3$ is a substituted norbornane group as defined in Table III, can be prepared as shown below (Method C). The process is described in detail in Example #30 (Method C-ii).

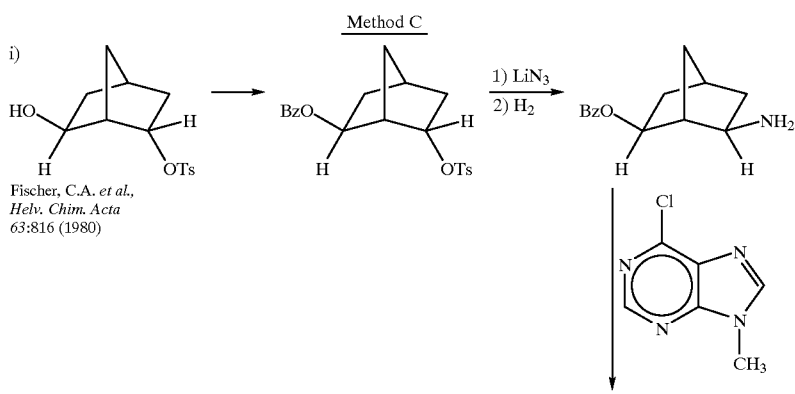

Method C i) Fischer, C.A. et al., Helv. Chim. Acta 63:816 (1980)

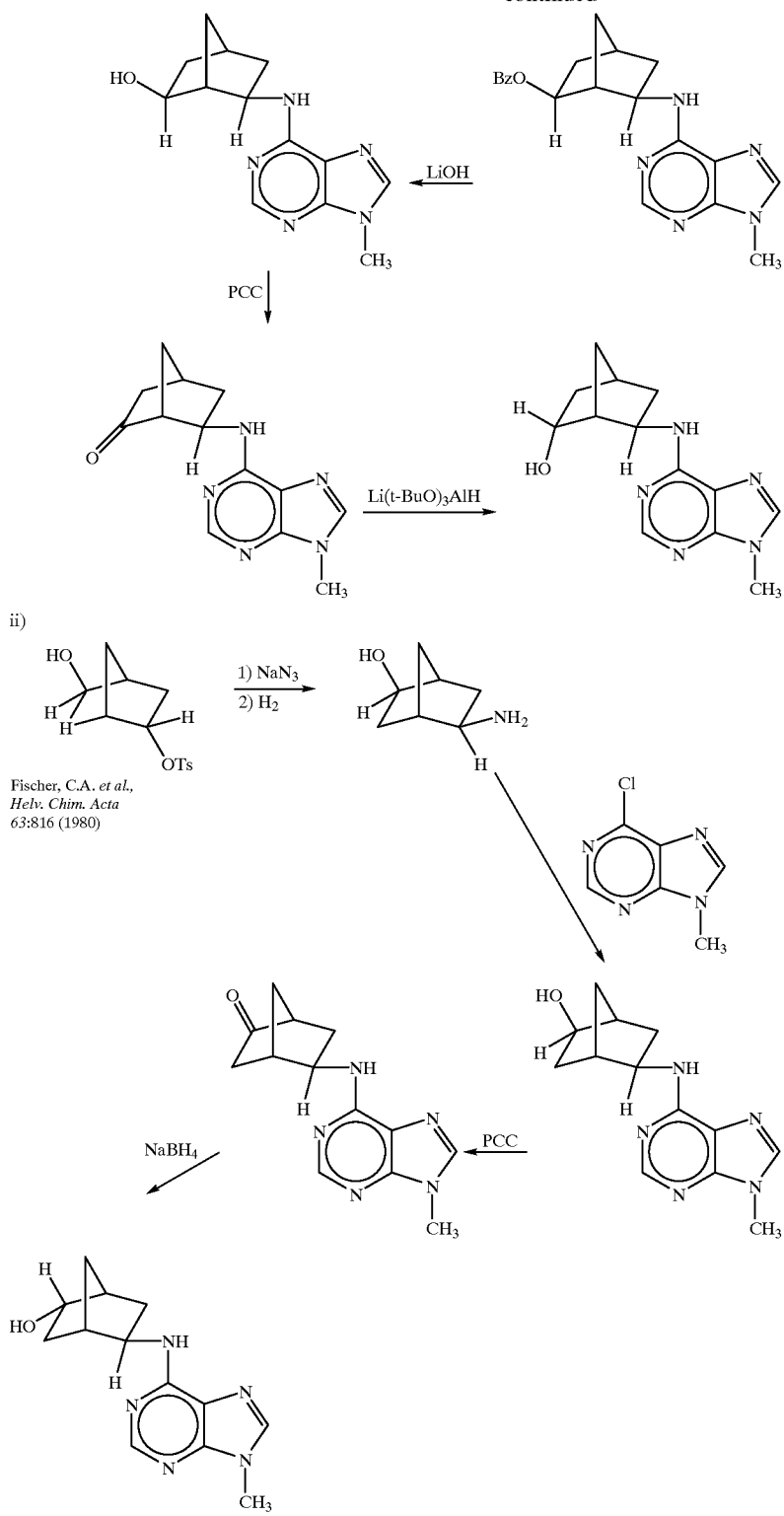

In the above method, pyridinium chlorochromate is abbreviated as "PCC".

Method C—Detailed Example: Preparation of (±)-N$^6$-[exo-2',(exo-5'-hydroxy)-norbornyl]-9-methyladenine.

A. exo-2'-amino,exo-5'-hydroxynorbornane. A mixture of 9.9 gm (0.035 mol) the exo-2-hydroxy-5-endo-tosyloxynorbornane and 11.4 gm (0.175 mol) of sodium azide in 90 ml of dry dimethylformamide was heated to 80° C. with stirring under nitrogen. After 28 h, the reaction mixture was concentrated, and the residue was partitioned between water and dichloromethane. The organic material was separated and the aqueous phase was re-extracted with dichloromethane, whereupon the organic extracts were pooled, dried (MgSO$_4$), and concentrated to 5 gm of product.

B. (±)-N6-[exo-2', (exo-5'-hydroxy)-norbornyl]-9-methyladenine. A solution of above product in 25 ml of dry tetrahydrofuran was slowly added to 33 ml of a 1 M solution of lithium aluminum hydride in tetrahydrofuran. Upon completion of addition, the mixture was stirred overnight, whereupon the mixture was treated with 1.5 ml of water, then with 1.5 ml of 6 N sodium hydroxide and 4.5 ml of water. The resulting mixture was filtered, concentrated and used directly in the next step.

C. The amine product in B) was reacted with 6-chloro-9-methylpurine substantially according to step B) in the detailed example for Method B. Isolation included flash chromatography, using ethyl acetate initially, then ethyl acetate/methanol (8:2) as eluting solvents. Concentration of appropriate fractions gave 100 mg of pure product.

TABLE III

| Example | R' | Empirical Formula | Elemental Analysis (calc./obs.) |
|---|---|---|---|
| 30 | 5'-exo-OH | $C_{13}H_{17}N_5O$ | C: 60.21/60.04 |
|  |  |  | H: 6.61/6.61 |
|  |  |  | N: 27.01/27.00 |
| 31 | 5'-endo-OH | $C_{13}H_{17}N_5O$ | C: 60.21/60.18 |
|  |  |  | H: 6.61/6.62 |
|  |  |  | N: 27.01/26.80 |

TABLE III-continued

| Example | R' | Empirical Formula | Elemental Analysis (calc./obs.) |
|---|---|---|---|
| 32 | 6'-endo-OH | $C_{13}H_{17}N_5O$ | C: 60.21/59.86 |
|  |  |  | H: 6.61/6.73 |
|  |  |  | N: 27.01/26.68 |
| 33 | 5'-keto | $C_{13}H_{15}N_5O$/ ¼ H$_2$O | C: 59.64/59.57 |
|  |  |  | H: 5.97/6.20 |
|  |  |  | N: 26.75/26.38 |
| 34 | 6'-keto | $C_{13}H_{15}N_5O$ | C: 60.69/60.63 |
|  |  |  | H: 5.88/6.04 |
|  |  |  | N: 27.22/26.67 |
| 35 | 6'-exo-OH | $C_{13}H_{17}N_5O$/ ½ H$_2$O | C: 58.19/58.39 |
|  |  |  | H: 6.76/6.77 |
|  |  |  | N: 26.10/25.92 |

Compounds of the current invention wherein $R_3$ is defined as:

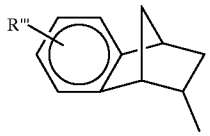

can be prepared as shown below (Method D). The process is described in detail for Example #36.

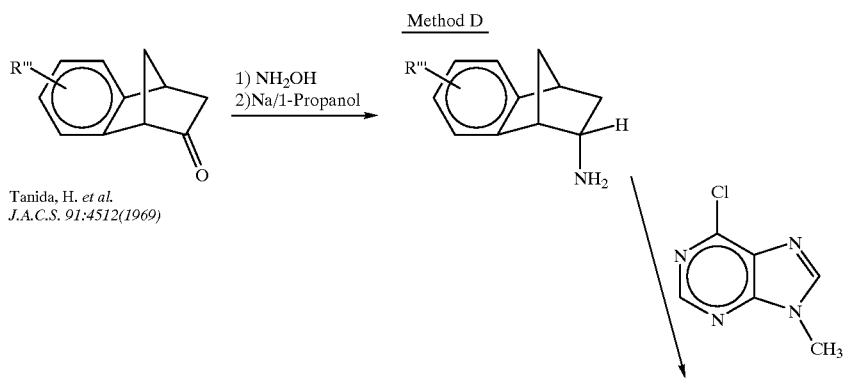

Tanida, H. et al.
J.A.C.S. 91:4512(1969)

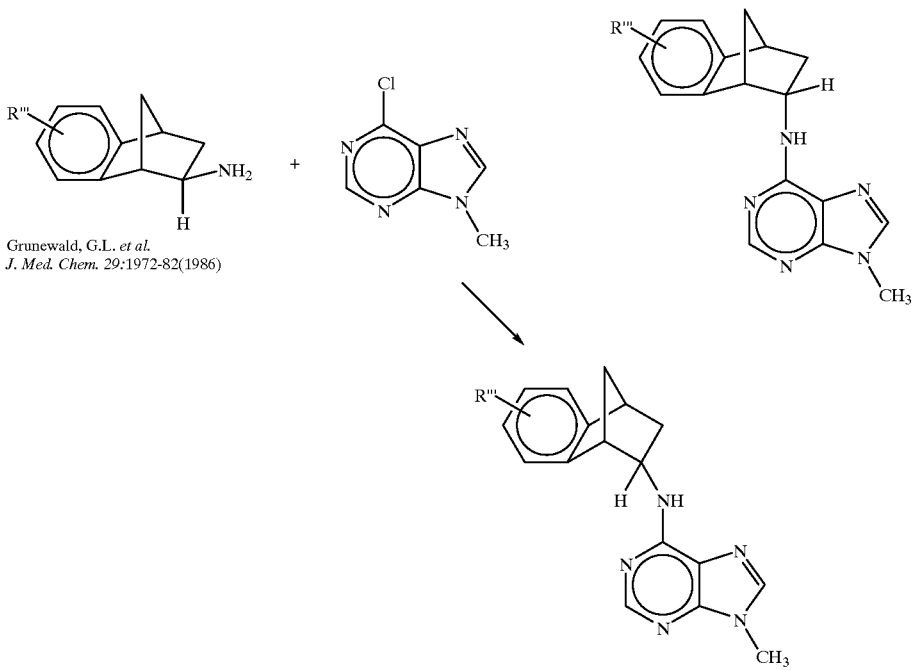

Grunewald, G.L. et al.
J. Med. Chem. 29:1972-82(1986)

Compounds where R'''=OH are prepared by cleavage of the methyl ethers by boron tribromide.

Method D—Detailed Example: Preparation of (±)-$N^6$-(exo-2'-amino-6'-6-hydroxybenzonorbornyl)-9-methyladenine.

A. (±)-$N^6$-(exo-2'-amino-6'-hydroxybenzonorbornyl)-9-methyladenine.

The following reactants were mixed and heated to reflux overnight under nitrogen: 440 mg (2.33 mmole) exo-2-amino-6-methoxybenzonorbornane, 392 mg (2.33 mmole) 6-chloro-9-methylpurine, 476 mg (4.7 mmole) triethylamine, 48 mg potassium iodide and 20 ml 1-propanol. The reaction mixture was then concentrated to a paste-like residue, which was partitioned between dichloromethane and water. Drying ($MgSO_4$) and concentration of the organic material gave an oil which was chromatographed (silica gel;ethyl acetate/methanol gradient ranging from 100% ethyl acetate to 95:5) to give the product, which was converted to the maleate salt (310 mg).

B. (±)-$N^6$-(exo-2'-amino-6'-hydroxybenzonorbornyl)-9-methyladenine.

The previous product (88 mg) was mixed with 2 ml dichloromethane and 0.7 ml (2.5 eq) of boron tribromide at −70° C. under nitrogen and stirred 30 minutes. The mixture was then allowed to come to room temperature, and refluxed for 1 hour. The reaction was quenched by the slow addition of 1 ml methanol with cooling. This was then concentrated, and after washing with isopropanol and saturated sodium bicarbonate, the resultant mixture was loaded on a desalting ion exchange XAD-2 column. Workup of the eluate provided the crystalline product.

TABLE IV

| Example | R''' | 2'-isomer | Empirical Formula | Elemental Analysis (calc./obs.) |
|---|---|---|---|---|
| 36 | 6'-OH | endo | $C_{17}H_{17}N_5O$/ HCl/ $H_2O$ | C: 56.50/56.65 H: 5.58/5.71 N: 19.38/19.38 |
| 37 | 6'-OH | exo | $C_{17}H_{17}N_5O$/ $C_4H_4O_4$/ ¼ $H_2O$/ ¼ EtOH | C: 58.76/58.69 H: 5.28/5.63 N: 15.94/16.23 |
| 38 | H | exo | $C_{17}H_{17}N_5$/ ¼ $H_2O$/ $C_4H_4O_4$ | C: 61.23/61.36 H: 5.26/5.10 N: 17.00/16.87 |
| 39 | H | endo | $C_{17}H_{17}N_5$/ $C_4H_4O_4$ | C: 61.91/62.20 H: 5.20/5.20 N: 17.19/17.05 |
| 40 | 6'-$OCH_3$ | exo | $C_{18}H_{19}N_5O$/ ¼ $H_2O$/ $C_4H_4O_4$ | C: 59.79/59.90 H: 5.36/5.25 N: 15.85/15.86 |
| 41 | 6'-$OCH_3$ | endo | $C_{18}H_{19}N_5O$/ $C_4H_4O_4$ | C: 60.41/60.13 H: 5.30/5.50 N: 16.01/15.96 |

Compounds of the present invention, where $R_1$ is not H, can be prepared substantially according to Method B, with the exception that instead of 9-methyl-6-chloropurine various 9-alkyl-6-chloropurines were used, which were prepared according to Robins, R., et al., *J. Am. Chem. Soc.* 79:490–4 (1957) by replacing methylamine with a desired alkylamine.

TABLE V

| Example | $R_1$ | R' | Empirical Formula | Elemental Analysis (calc./obs.) |
|---|---|---|---|---|
| 42 | —CH$_2$CH$_2$CH$_3$ | 5'-endo-OH | C$_{15}$H$_{21}$N$_5$O | C: 62.70/62.80<br>H: 7.37/7.50<br>N: 24.37/24.42 |
| 43 | —CH$_2$CH$_2$CH$_3$ | 5'-exo-OH | C$_{15}$H$_{21}$N$_5$O/<br>C$_4$H$_4$O$_4$ | C: 56.57/56.48<br>H: 6.25/6.19<br>N: 17.36/17.24 |
| 44 | —CH(CH$_3$)$_2$ | 5'-keto | C$_{15}$H$_{19}$N$_5$O | C: 63.14/63.18<br>H: 6.71/6.69<br>N: 24.54/24.50 |
| 45 | —CH(CH$_3$)$_2$ | 5'-endo-OH | C$_{15}$H$_{21}$N$_5$O | C: 62.70/62.84<br>H: 7.37/7.37<br>N: 24.37/24.54 |
| 46 | —CH(CH$_3$)$_2$ | 5'-exo-OH | C$_{15}$H$_{21}$N$_5$O/<br>C$_4$H$_4$O$_4$ | C: 56.57/56.70<br>H: 6.25/6.44<br>N: 17.36/17.25 |

Pharmacological Testing of Exemplified Compounds

Pharmacological test methods are described below. The compounds of the present invention were tested for adenosine antagonist activity, with results being summarized in the accompanying tables. These data were generated to provide measures of the compounds' selectivity ($A_1/A_2$) for adenosine $A_1$ receptors and their in vitro functional potency at adenosine $A_1$ receptors. Test results for comparative examples in the prior art (see Ukena, D., et al., *FEBS Lett.* 215:203–8 (1987); Thompson, R., et al., *J. Med. Chem.* 34:2877–82 (1991); Olsson, R., U.S. Pat. No. 5,066,655) are included for reference purposes (Example 47: $N^6$-cyclohexyl-9-methyladenine, Example 48: $N^6$-cyclopentyl-9-methyladenine, Example 49: $N^6$-(endo-2-norbornyl)-9-methyladenine).

1. Receptor Affinity Experiments (Radioligand Binding)

Tissues (bovine caudate, guinea pig cortex, guinea pig striatum) were homogenized with a Brinkman polytron and the membranes were collected by centrifugation at 40,000×g at 4° C. for 10 min. The membranes were washed by resuspension and centrifugation, resuspended, and incubated in the presence of 1 U/ml adenosine deaminase for 15–30 min. at 37° C. The membranes were diluted, centrifuged once, and resuspended to a final concentration of 0.5–2 mg protein/ml. Adenosine deaminase (0.1 U/ml) was included in the final resuspension. Assays were initiated by addition of membranes. The compounds of the present invention were subjected to the following experimental conditions: $A_1$ determinations/incubated with [$^3$H]CHA at room temperature for 2 hours, $A_2$ determinations/incubated with [$^3$H] NECA at room temperature for 1 hour. Assays were terminated by filtration, and the filters were counted in scintillation counters. Data were analyzed using the Ligand program of Munson and Rodbard (1980), and the results are presented in Table VI below:

TABLE VI

Adenosine $A_1$ and $A_2$ Receptor Affinity and Resultant Selectivity Ratio

| Example | $A_1K_i$ ($\mu$M) | $A_2K_i$ ($\mu$M) | Selectivity Ratio ($A_2K_i/A_1K_i$) |
|---|---|---|---|
| 1 | 0.00389 | 1.41 | 362 |
| 2 | 0.0129 | 3.55 | 275 |
| 3 | 0.00603 | 0.398 | 66 |
| 4 | 0.0120 | 0.513 | 43 |
| 5 | 0.00371 | 0.617 | 166 |
| 6 | 0.0240 | >10 | >417 |
| 7 | 0.0190 | >10 | >526 |
| 8 | 0.00617 | 1.35 | 219 |
| 9 | 0.00794 | 10 | 1,259 |
| 10 | 0.00100 | 0.331 | 331 |
| 11 | 0.0458 | 11 | 240 |
| 12 | 0.00250 | 0.363 | 145 |
| 13 | 0.00631* | 1.05 | 166 |
| 14 | 0.00372 | 0.436 | 117 |
| 15 | 0.0420 | >10 | >238 |
| 16 | 0.0000891 | 0.234 | 2,626 |
| 17 | 0.00117 | 0.0692 | 59 |
| 18 | 0.00275 | 0.275 | 100 |
| 19 | 0.00347 | 0.347 | 100 |
| 20 | 0.191 | >10 | >52 |
| 21 | 0.191 | 3.16 | 165 |
| 22 | 0.0977 | 31.6 | 323 |
| 23 | 0.0851 | 31.6 | 371 |
| 24 | 0.141 | 21.4 | 152 |
| 25 | 0.0190 | >10 | >526 |
| 26 | 0.00955 | 5.75 | 602 |
| 27 | 0.00501 | 0.661 | 132 |
| 28 | 0.00831 | 4.57 | 550 |
| 29 | 0.501 | >10 | >20 |
| 30 | 0.0363 | 42.7 | 1,176 |
| 31 | 0.105 | 14.4 | 137 |
| 32 | 0.0513 | >10 | >195 |
| 33 | 0.0427 | 11.5 | 269 |
| 34 | 0.0692 | 15.1 | 218 |
| 35 | 0.295 | 35.5 | 120 |
| 36 | 0.00200 | 0.631 | 316 |
| 37 | 0.0115 | 4.57 | 397 |
| 38 | 0.0178 | 5.89 | 331 |
| 39 | 0.468 | 15.5 | 33 |
| 40 | 0.00891 | 5.62 | 631 |
| 41 | 0.209 | >10 | >48 |
| 42 | 0.0288 | 6.46 | 224 |
| 43 | 0.257 | >10 | >39 |
| 44 | 0.251 | 21.4 | 85 |
| 45 | 0.295 | >10 | >34 |
| 46 | 0.295 | >10 | >34 |
| 47 | 0.0457 | 11.0 | 241 |
| 48 | 0.0100 | 5.01 | 501 |
| 49 | 0.0100 | 6.17 | 617 |

*This value was obtained using guinea pig tissue.

These data show the high degrees of adenosine A, receptor affinity and selectivity achieved with compounds of the current invention.

2. Adenosine—$A_1/A_2$ In Vitro Functional Tests ($A_1$ Assay: Negative inotropic response)—Guinea pig left atria were placed in organ baths filled with Krebs Henseleit solution gassed with 95% $O_2$ and 5% $CO_2$ and maintained at a temperature of 31° C. An initial resting tension of 1 gm. was placed on each tissue, which was allowed to equilibrate. Atria were stimulated electrically to produce twitch responses. A dose-response curve for the inhibition of the electrically-evoked twitch response was obtained by cumulative addition of the adenosine agonist 5'-N- ethylamidoadenosine. After the washout of the tissue, a fixed concentration of test compound was added and the tissue allowed to equilibrate for 1 hr. before cumulative additions of the adenosine agonist 5'-N-ethylcarboxamidoadenosine (NECA) to generate a new dose response curve. This procedure was repeated with different fixed concentrations of test compounds to generate a family of dose response curves. Schild plots were constructed from the resultant concentration-effect curves, and $K_B$ (antagonist dissociation constant) values were obtained. The results (see Table VII) are expressed as $K_B$ values (concentration of test compound such that one-half of the tissue adenosine receptor population is occupied by the test compound).

($A_2$ Assay: Vasodilation)—Guinea pig isolated thoracic aorta were cut into ring segments and placed between parallel wires for the measurement of isometric force in the above solution at 37° C. An initial resting tension of 2 gm. was placed on each tissue, which was then allowed to equilibrate for 1 hour. Phenylephrine (3 $\mu$M) was added to each tissue to produce a contractile response, and once this was obtained the test compound was added and allowed to equilibrate for 1 hour. A concentration-effect curve was produced by the addition of NECA at 0.5 M unit increments. Responses were expressed as the percentage inhibition of phenylephrine-induced contractions. Data analysis was performed in an analogous way as the $A_1$ assay above, with results expressed as $K_B$ values.

TABLE VII

Functional Potencies at Adenosine $A_1$ and $A_2$ Receptors and Resultant Selectivity Ratio

| Example | $A_1K_B$ ($\mu$M) | $A_2K_B$ ($\mu$M) | Selectivity Ratio ($A_2K_B/A_1K_B$) |
|---|---|---|---|
| 1 | 0.081 | 3.71 | 46 |
| 2 | 0.257 | >100 | >390 |
| 3 | 0.065 | >100 | >1540 |
| 4 | 0.105 | 26.3 | 250 |
| 5 | 0.110 | 39.8 | 362 |
| 8 | 0.501 | — | — |
| 10 | 0.117 | — | — |
| 12 | 0.071 | — | — |
| 13 | 0.005 | >100 | >20000 |
| 16 | 0.004 | 4.75 | 4450 |
| 17 | 0.030 | 1.95 | 65 |
| 18 | 0.072 | — | — |
| 19 | 0.115 | — | — |
| 20 | 0.240 | — | — |
| 21 | 0.309 | >100 | 324 |
| 22 | 2.95 | — | — |
| 23 | 3.80 | — | — |
| 24 | 4.68 | — | — |
| 30 | 1.31 | — | — |
| 31 | 4.07 | — | — |
| 32 | 6.03 | — | — |
| 36 | 0.275 | — | — |
| 38 | 1.58 | — | — |
| 39 | 28.8 | — | — |
| 40 | 1.12 | — | — |
| 41 | 64.6 | — | — |
| 47 | 2.08 | >316 | >152 |
| 48 | 0.759 | >300 | >395 |
| 49 | 0.550 | 19.9 | 36 |

These data show the high degrees of adenosine $A_1$ receptor in vitro functional activity and selectivity ($A_1$ vs. $A_2$).

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the formula

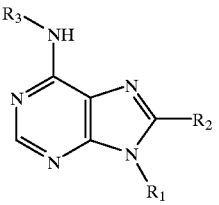

or a pharmaceutically acceptable salt thereof;
where $R_1$ is $C_1$ to $C_4$ straight chain or branched chain alkyl; $R_2$ is selected from the group consisting of H, —$OR_1$, —$SR_1$, —$N(R_4)(R_5)$, aminocarbonyl, halogen, and —CN, where $R_4$ is methyl and $R_5$ is isopropyl, or $R_4$ and $R_5$ taken together with the N to which they are attached form a 3- to 7-membered heterocycle, said heterocycle optionally including an additional heteroatom which is selected from the group consisting of nitrogen, oxygen and sulfur; $R_3$ is cyclopentyl or:

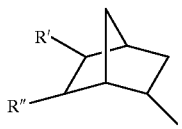

where R' and R" are independently H, =O, —OH, or —NH, or R' and R" can be taken together to form the following structure as $R_3$:

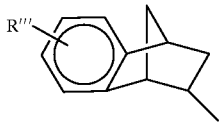

where R'" is —OH or —$NH_2$; with the proviso that when $R_3$ is cyclopentyl or norbornyl, then $R_2$ cannot be H or halogen.

2. A compound having the formula:

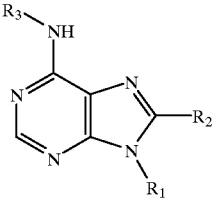

or a pharmaceutically acceptable salt thereof; where
$R_1$ is $C_1$ to $C_4$ straight chain or branched alkyl;
$R_2$ is selected from the group consisting of —$OR_1$, —$SR_1$, —$N(R_4)(R_5)$, aminocarbonyl, and —CN, where
$R_4$ is methyl and $R_5$ is isopropyl, or $R_4$ and $R_5$ taken together with the nitrogen to which they are attached form a heterocyclic substituent selected form the group consisting of aziridinyl, piperidinyl, piperazinyl, imidazolidinyl, pyrrolidinyl, imidazolinyl, morpholinyl, pyrazolidinyl and pyrazolinyl;

$R_3$ is cyclopentyl or norbornyl.

3. The compound of claim 1, wherein $R_3$ is cyclopentyl.

4. The compound of claim 3, wherein $R_1$ is methyl.

5. The compound $N^6$-(endo-2'-norbornyl)-8-dimethylamino-9-methyladenine.

6. The compound $N^6$-(endo-2'-norbornyl)-8-diethylamino-9-methyladenine.

7. The compound of claim 1, which is $N^6$-(endo-2'-norbornyl)-8-isopropylmethylamino-9-methyladenine.

8. The compound of claim 1, wherein $R_2$ is H, —NH($R_1$), —N($R_4$)($R_5$), —O$R_1$, —S$R_1$, halogen, or —CN.

9. The compound of claim 2, wherein $R_2$ is —N($R_4$)($R_5$).

10. The compound of claim 1, wherein $R_2$ is methylthio or methoxy.

11. The compound (±)-$N^6$-[endo-2'-norbornyl]-8-isopropylmethylamino-9-methyladenine, or a pharmaceutically acceptable salt thereof.

12. A pharmaceutical composition, comprising the compound of claim 1 and a pharmaceutically acceptable carrier.

13. The compound of claim 2, which is $N^6$-cyclopentyl-8-isopropylmethylamino-9-methyladenine.

* * * * *